United States Patent
Palmer, Jr. et al.

(10) Patent No.: US 10,206,899 B2
(45) Date of Patent: Feb. 19, 2019

(54) METHOD FOR REMOVING BACTERIAL BIOFILMS

(71) Applicant: Infection Elimination Services, LLC, Pelzer, SC (US)

(72) Inventors: Charles Francis Palmer, Jr., Pelzer, SC (US); Thomas William Campbell, Jr., Pelzer, SC (US)

(73) Assignee: Infection Elimination Solutions, LLC, Pelzer, SC (US)

( * ) Notice: Subject to any disclaimer, the term of this patent is extended or adjusted under 35 U.S.C. 154(b) by 0 days.

(21) Appl. No.: 15/247,455

(22) Filed: Aug. 25, 2016

(65) Prior Publication Data

US 2018/0055808 A1    Mar. 1, 2018

(51) Int. Cl.
*A61K 31/22*    (2006.01)
*A61K 31/225*   (2006.01)
*A61K 31/255*   (2006.01)

(52) U.S. Cl.
CPC ............ *A61K 31/255* (2013.01); *A61K 31/22* (2013.01); *A61K 31/225* (2013.01)

(58) Field of Classification Search
CPC ..... A61K 31/22; A61K 31/225; A61K 31/255
See application file for complete search history.

(56) References Cited

U.S. PATENT DOCUMENTS

| 6,723,688 B1 * | 4/2004 | Malik | A61K 8/442 510/130 |
| 2014/0072519 A1 * | 3/2014 | Sharma | A61K 8/347 424/56 |

FOREIGN PATENT DOCUMENTS

WO    WO 2006065239    *    6/2006

\* cited by examiner

*Primary Examiner* — Shirley V Gembeh
(74) *Attorney, Agent, or Firm* — Joseph T. Guy; Patent Filing Specialist, Inc.

(57) ABSTRACT

A treatment mixture for treating biofilms on a human or animal is provided. The treatment mixture comprises:
an effective amount of a salt of alkyleth sulfate defined by Formula I:

$$R^1\text{—}(OCHR^2CH_2)_n\text{—}OSO_3X^1 \quad \text{Formula I}$$

wherein:
$R^1$ is a branched or unbranched alkyl of 8-24 carbons;
$R^2$ is hydrogen or methyl;
n is an integer of 2 to 30; and
each $X^1$ is independently a counter ion;
an effective amount of at least one surfactant selected from the group consisting of a salt of alkyl sulfoacetate defined by Formula II:

$$R^4OC(O)CH_2SO_3X^2 \quad \text{Formula II}$$

wherein $R^4$ is a branched or unbranched alkyl of 8-24 carbons; and
$X^2$ is a counter ion;
and an effective amount of a salt of an alkyl sulfosuccinate defined by Formula III:

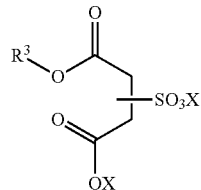

Formula III wherein:
$R^3$ is the branched or unbranched alkyl group of an alkyl alcohol with the alcohol hydrogen replaced with the sulfosuccinate wherein the alkyl has of 8-24 carbons, more preferably 10-18 carbons and most preferably 12-14 carbons; and
X is a counter ion.

43 Claims, No Drawings

METHOD FOR REMOVING BACTERIAL BIOFILMS

BACKGROUND

This invention is related to methods for improving the healing rate of infected wounds or sores on humans or animals, that are otherwise slow to heal, by usual treatment methods. More specifically, the present invention is related to a mixture of surfactants and their use in removing biofilms, especially those from body tissue or materials in contact with body tissue such as implants.

The historical view of bacteria is that they are free-living organisms easily kept in check by antibiotics, however, scientists are now realizing that bacteria spend most of their lives in colonies, or biofilms, even in the human body. Biofilms are communities of bacteria in self-produced slime and may be found almost anywhere that solids and liquids meet, whether in nature, in hospitals or in industrial settings. According to the United States' Centers for Disease Control, biofilms are implicated in more than 80% of chronic inflammatory and infectious diseases caused by bacteria, including ear infections, gastrointestinal ulcers, urinary tract infections and pulmonary infections in cystic fibrosis patients. It is widely thought that in their natural habitat most bacteria live as a community and attach to surfaces as biofilms and that many infections in humans are related to biofilms. While single bacteria may be treatable with antibiotics, the films can be 1,000 times more resistant and most can only be removed surgically.

Bacteria that form biofilms occasionally infect implants such as pacemakers, stents, and artificial joints. These biofilm sites periodically shed bacteria, often referred to in the art as adventurers, which can ignite acute infections and fever. While antibiotics can knock out these free-swimming bacteria and temporally calm down the infection, the biofilm remains untouched. The only permanent solution is removal of the biofilm-coated device and replacement with a new sterilized implant.

A permanent bacterial biofilm in the sinuses can ignite an immune response leading to chronic sinus infections, with symptoms including fever and cold-like symptoms. So far, the most effective treatment is to surgically remove the affected tissue.

Bacteria also form permanent, mostly lifelong, biofilms in the mucus-filled lungs of cystic fibrosis patients and are responsible for the chronic lung infections that lead to early death. Although long-lasting antibiotic treatment helps, it cannot eradicate the infection completely.

Biofilms are difficult to eradicate with conventional antimicrobial treatments since they are far more resistant to antibiotics than planktonic, or free-floating adventurer cells. Biofilms also pose a persistent problem in many industrial processes, including drinking water distribution networks and manufacturing environments.

The problem with a chronic infection is that the immune system attempts to clear the infection but is unable to. The longer the chronic infection goes on, the more damage there will be to tissue at the site of the infection because the immune response often involves the release of toxic compounds that have no effect on biofilms but can damage the surrounding tissues.

In one reported observation, over a period of about six hours, a single bacterium laid down a glue to attach itself to a surface, then divided into daughter cells, making certain to cement each daughter to itself before splitting in two. The daughters continued to divide until they formed a cluster, like a brick and mortar building, at which point the bacteria secreted a protein encasing the cluster like the shell of a building. The clusters are separated by micro-channels that may allow nutrients in and waste out.

Bed sores, also known as pressure ulcers, pressure sores, or decubitus ulcers are skin lesions which can be caused by friction, humidity, temperature, incontinence, medication, shearing forces, age and unrelieved pressure. Any part of the body may be affected, however, bony or cartilaginous areas, such as the elbows, knees, ankles and sacrum are most commonly affected. If discovered early, bedsores are treatable. However, they may sometimes be fatal. According to health authorities in the UK and USA, bedsores are the second iatrogenic cause of death, after adverse drug reactions causing hospitals to spend about $5 billion annually for treatment of pressure ulcers.

Biofilms are one of the most common reasons for delayed healing in pressure ulcers. Biofilm formation occurs rapidly in wounds and stalls healing by keeping the wound inflamed. Frequent debridement and antimicrobial dressings are needed to control the biofilm. Infection prevents healing of pressure ulcers. Symptoms of infection in a pressure ulcer include slow or stalled healing and pale granulation tissue. Infection can expand from local to systemic. Symptoms of systemic infection include fever, pain, redness, swelling, warmth of the area, and purulent discharge. Additionally, infected wounds may have a gangrenous smell, be discolored, and may eventually exude even more pus. In order to eliminate this problem, it is imperative to apply antiseptics at once. Hydrogen peroxide, a near-universal toxin, is not recommended for this task as it increases inflammation and impedes healing. Systemic antibiotics are not recommended in treating local infection in a pressure ulcer, as it can lead to bacterial resistance. They are only recommended if there is evidence of advancing cellulitis, osteomyelitis, or bacteremia.

Surfactants with detergency are known to remove a number of water insoluble materials from hard surfaces such as oily materials, grassy materials, proteinaceous materials and dirt based materials. Surfactants are usually organic compounds that are amphiphilic, meaning they contain both hydrophobic moieties, often referred to as their tails, and hydrophilic moieties, often referred to as their heads. Surfactants will diffuse into water and adsorb at interfaces between air and water or at the interface between oil and water, in the case where water is mixed with oil. The water-insoluble hydrophobic group may extend out of the bulk water phase, into the air or into the oil phase, while the water-soluble head group remains in the water phase.

Detergents have also been used to decellularise organs with limited success. This process maintains a matrix of proteins that preserves the structure of the organ and often the microvascular network. The process has been successfully used to prepare organs such as the liver and heart for transplant in rats. Pulmonary surfactants are also naturally secreted by type II cells of the lung alveoli in mammals.

Other approaches toward treating biofilms are known. U.S. Pat. No. 8,753,662 teaches methods of inhibiting biofilm formation or reducing biofilms in a subject or on a device or surface by administering a charged compound such as a polyamino acid to a subject, device or surface. The invention also relates to compositions for inhibiting biofilm formation or reducing biofilms. U.S. Pat. No. 8,748,617 discloses the use of amide compounds or salts thereof and biofilm inhibitor, biofilm remover, and disinfectant containing the same. The disclosure provides an amide compound and salt thereof that is capable of inhibiting biofilm formation or removing deposited biofilms. U.S. Pat. No. 8,747,872 relates to methods and compositions for treating pulmonary infection. In particular, it provides nanoemulsion compositions and methods of using the same to treat bacteria associated with biofilms such as those found in pulmonary infections. Compositions and methods of the invention find use in, among other things, clinical settings for use as therapeutic and preventative medicine, industrial applications, and research applications.

The prior art cited above shows materials designed to kill bacteria or inhibit biofilm formation. It also shows that certain detergent surfactants are known to lyse cell membranes and tissues by disorganizing the membrane's lipidic bilayer, which would damage healthy tissue, however, they are marginally effective. The milder detergents disclosed in the art such as octyl thioglucoside, octyl glucoside or dodecyl maltoside that are used to solubilize membrane proteins such as enzymes and receptors without denaturing them are expensive and not widely available.

It is clear that there is a need for an effective method to remove bacterial biofilms, especially those in bedsores or on implants, to reduce the mortality rate due to infections, both internal and external to the body. Further, a method that avoids systemic antibiotics would have advantages of lower treatment cost, the avoidance of adverse reactions to the medications, and avoid the development of bacterial resistance to antibiotics. A nonsurgical method to remove biofilms would likely have lower treatment costs, reduced risk of complications, and reduced need to remove healthy tissue along with the infected tissue.

In spite of the ongoing effort there is still a desire for a method of disrupting biofilms thereby releasing the bacteria therefrom to allow natural mitigation of infection or increased access to systemic or localized antibiotics. Such an improvement is provided herein.

SUMMARY OF THE INVENTION

It is an object of the invention to provide a method for disrupting biofilms.

It is another object of the invention to provide a method for disrupting biofilms without adverse effect on surrounding healthy tissue.

A particular feature of the present invention is the simplicity in use which does not require significant medical training and can be done by a patient or untrained care provider.

These and other embodiments, as will be realized, are provided in a treatment mixture for treating biofilms on a human or animal comprising: an effective amount of a salt of alkyleth sulfate defined by Formula I:

   $R^1$—$(OCHR^2CH_2)_n$—$OSO_3X^1$     Formula I wherein:
$R^1$ is a branched or unbranched alkyl of 8-24 carbons;
$R^2$ is hydrogen or methyl;
n is an integer of 2 to 30; and
each $X^1$ is independently a counter ion;
an effective amount of at least one surfactant selected from the group consisting of a salt of alkyl sulfoacetate defined by Formula II:

$R^4OC(O)CH_2SO_3X^2$     Formula II wherein $R^4$ is a branched or unbranched alkyl of 8-24 carbons; and
$X^2$ is a counter ion;
and an effective amount of a salt of an alkyl sulfosuccinate defined by Formula III:

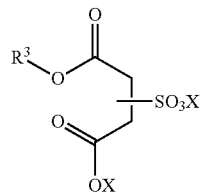
                       Formula III wherein:
$R^3$ is the branched or unbranched alkyl group of an alkyl alcohol with the alcohol hydrogen replaced with the sulfosuccinate wherein the alkyl has of 8-24 carbons, more preferably 10-18 carbons and most preferably 12-14 carbons; and
X is a counter ion.

Yet another embodiment is provided in a method for the removal of bacterial biofilms comprising:
applying a treatment mixture to said biofilm wherein said treatment mixture comprises:
an effective amount of a salt of alkyleth sulfate defined by Formula I:

$R^1$—$(OCHR^2CH_2)_n OSO_3X^1$     Formula I wherein:
$R^1$ is a branched or unbranched alkyl of 8-24 carbons;
$R^2$ is hydrogen or methyl;
n is an integer of 2 to 30; and
each $X^1$ is independently a counter ion;
an effective amount at least one surfactant selected from the group consisting of a salt of alkyl sulfoacetate defined by Formula II:

$R^4OC(O)CH_2SO_3X^2$     Formula II wherein $R^4$ is a branched or unbranched alkyl of 8-24 carbons; and
$X^2$ is a counter ion;
and a salt of an alkyl sulfosuccinate defined by Formula III:

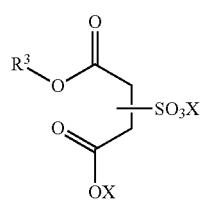
                       Formula III wherein:
$R^3$ is the branched or unbranched alkyl group of an alkyl alcohol with the alcohol hydrogen replaced with the sulfosuccinate wherein the alkyl has of 8-24 carbons, more preferably 10-18 carbons and most preferably 12-14 carbons; and
X is a counter ion;
treating said biofilm to at least one procedure selected from the group consisting of rinsing with water and allowing said biofilm to dry; and
re-applying a treatment mixture to said biofilm.

DESCRIPTION

The instant invention is directed to an improved method for removing bacterial biofilms which is particularly suitable for treating infected wounds or implants. More specifically, the present invention is directed to a mixture of surfactants which is effective in the disruption of the biofilm matrix thereby allowing for the release of bacteria for subsequent treatment.

While not limited to any theory, the treatment mixture of the present invention provides a mixture of surfactants which is believed to disrupt and disperse the biofilm thereby allowing the body's natural defenses to attack the released bacteria. Alternatively, the released bacteria are more readily treatable with antibiotics either systemically or locally applied.

The treatment mixture comprises active components with an ethoxylated component defined by Formula I and at least one of Formula II or Formula III and preferably both Formula II and Formula III. Formula I is a salt of alkyleth sulfate defined by:

$$R^1-(OCHR^2CH_2)_nOSO_3X^1 \quad \text{Formula I}$$

wherein:
  $R^1$ is a branched or unbranched alkyl of 8-24 carbons, more preferably 10-18 carbons and most preferably 12-14 carbons;
  $R^2$ is hydrogen or methyl;
  n is an integer of 2 to 30, preferably 4-10;
  each $X^1$ is independently a counter ion preferably selected from alkali metal or ammonium and preferably sodium or potassium;
  Formula II is a salt of an alkyl sulfoacetate defined by:

$$R^4OC(O)CH_2SO_3X^2 \quad \text{Formula II}$$

wherein $R^4$ is a branched or unbranched alkyl of 8-24 carbons, more preferably 10-18 carbons and most preferably 12-14 carbons;
  and $X^2$ is a counter ion preferably selected from alkali metal and preferably sodium or potassium;
  Formula III is a salt of an alkyl sulfosuccinate defined by:

Formula III

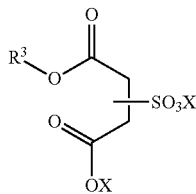

wherein:
  $R^3$ is the branched or unbranched alkyl group of an alkyl alcohol with the alcohol hydrogen replaced with the sulfosuccinate wherein the alkyl has 8-24 carbons, more preferably 10-18 carbons and most preferably 12-14 carbons, and
  each X is independently a counter ion preferably selected from alkali metal metal or ammonium and preferably sodium or potassium.

Though not limited to any theory, the ethoxy groups of Formula I are believed to facilitate rupture of the cell membranes of the biofilm thereby allowing the other components, represented by Formula II and Formula III, to more effectively solubilize and disperse the fragmented biofilm. A particularly preferred compound of Formula I is sodium laureth sulfate.

A particularly preferred compound of Formula II is sodium lauryl sulfoacetate.

A particularly preferred compound of Formula III is disodium lauryl sulfosuccinate.

The treatment mixture is preferably an aqueous solution and may comprise additional adjuvants such as humectants or hygroscopic materials; rheology aids such as foam enhancers or foam stabilizers; acids or bases to adjust pH; chelates or chelating agents; preservatives to inhibit microbial growth such as antimicrobial medicines or antibiotic; viscosity control agents or additional surfactant.

While not limited to theory, humectants are believed to assist in wetting the biofilm thereby improving the ability of the active components to disrupt and disperse the biofilm. Hygroscopic materials can impart a moisturizing effect to the treated tissues and by attracting water may improve the removal of the biofilms by subsequent rinsings. Polyols and polyethoxylated polyols are particularly preferred humectants. Particularly preferred polyols include sorbitol, glycerine, and other simple sugars. Particularly preferred polyethoxylated polyols include glycereth-26 (polyethylene 26 glycerin), sorbitol ethoxylate, and polyethylene glycol.

Rheology aids assist in controlling the viscosity, or rheology, of the treatment mixture thereby optimizing residence time of the treatment mixture at the site of the biofilm. In some applications the treatment mixture may have a low viscosity suitable for application as a flowing liquid or spray. In other applications the treatment mixture may have a higher viscosity for application as a gel or cream which remains at the site with minimal flowing until rinsed. In other applications the treatment mixture may foam thereby insuring a longer residence time with optional effervescence to provide refreshment of active components. Foam stabilizers are known to stabilize foams and the foam strength may be related to biofilm removal efficacy. Sorbitol, glycerin, and ethoxylated glycerin or sorbitol are some suitable hygroscopic and foam stabilizing additives. Thickeners or other viscosity control agents may be added to gel the surfactant mixture to hold it in place on the sore. The treatment mixture may be rheological having shear thinning properties thereby allowing for spray applications, such as through a nozzle, with higher viscosity after application for increased residence time. Particularly preferred rheology aids include foam enhancers such as cocoamidopropyl betaine, cocoamide, cocoamide MEA, and cocoamide DEA.

The pH of the treatment mixture can be adjusted by acids and bases wherein the acid or base may have additional functionality such as functioning as a chelating agent. Particularly preferred acids and bases are those that are biologically inert. Lactic, citric, and ascorbic acids are a particularly suitable acids for lowering pH and tetrasodium ethylenediaminetetraacetic acid (EDTA) and sodium citrate are particularly suitable bases for raising pH.

The treatment mixture may include stabilizers and preservatives, particularly, if microbial growth of the mixture is a concern or for storage or transport. Antimicrobial medicines or antibiotics to kill the bacteria or other microbes present may speed wound healing. Particularly preferred stabilizers or preservatives include imidazolidinyl urea, parabens, methylchloroisothiazolinone, and methylisothiazolinone. Topical antibiotics are most preferred. Particularly suitable antibiotics include bacitracin zinc, neomycin sulfate, and polymyxin B sulfate.

The concentration of active components can be relatively low and still be effective. A concentration effective amount is about 0.025 wt % to about 30 wt % solids in water with solids being the total sum of the active components. Adjuvants are preferably about 0.025 wt % to about 20 wt %. Below 0.025 wt % active components the effectiveness of the mixture is insufficient to disrupt the biofilm at a reasonable rate thereby requiring excess flow of material. Above about 30 wt % active components the room temperature viscosity is too high to easily handle the product and the volume of water is insufficient to solubilize and remove the disrupted material. The concentration of active components in the treatment solution should be chosen so that they are effective at removing the biofilm in a small number of rinsings, but not so concentrated as to cause excessive irritation or damage to the nearby human tissue. A concentration of at least about 5 wt % active component to no more than about 15 wt % is preferred with about 10 wt % of active components being optimal for most applications. The concentration for subsequent rinsings may be adjusted up or down as desired. A higher concentration of surfactant will increase the detergency and rate of biofilm removal or destruction, but will increase the chance of healthy tissue irritation or damage.

The treatment mixture is suitable for use in a method for removal of bacterial biofilms from living tissue and hard surfaces by physical removal through the action of a mild surfactant solution in a water-based cleansing solution. This biofilm removal method is effective yet inexpensive, based on readily available surfactants, leaves peripheral patient tissue largely unaffected by the treatment, and is very gentle and well tolerated by the patient.

The present invention is a method for increasing the rate of healing of sores on humans or animals, especially pressure sores, comprising the application of an effective amount of an aqueous solution of surfactants for a length of time suitable to effect a cure. Not wishing to be bound by conjecture, it is believed that the efficacy of the inventive surfactant mixture is largely due to its ability to destroy and/or remove the biofilm from the sore and allow the body's healing mechanisms to function unimpeded by the biofilm and the bacterial toxins.

It is expected that different sores will have different biofilms, and thus the amount of treatment surfactant mixture, its concentration, and length of treatment time to destroy the biofilm and promote healing will vary. In addition, other factors related to wound healing rates such as blood supply, depth of the sore, health of the individual, etc., will affect the rate of healing.

The biofilm removal may take more than one application of surfactant solution, different methods of surfactant application, and may take several days of treatments. The surfactants are chosen to be effective in removing the biofilm as well as to minimize adverse effects to the living non-bacterial tissue adjoining the biofilm.

Suitable surfactants for use in the treatment mixture and combinations thereof preferably exhibit both low toxicity and irritation. They must also not destroy the human tissue near the biofilm to be removed. Some anionic surfactants that function well to assist in the removal of biofilms include alcohol ethoxylate sulfates, alcohol sulfoacetates, and alcohol ethoxylate sulfosuccinates that are used in personal care applications. Anionic alcohol sulfates, alcohol ethoxylate carboxylates, or sulfonates may also be effective. These anionic surfactants are chosen to assist in effective biofilm removal or destruction and cause little irritation or damage to healthy tissue. In a preferred embodiment a small amount of treatment mixture is applied to a portion of tissue which is not infected to insure no reaction will occur.

Nonionic or amphoteric surfactants may be combined with the treatment mixture to improve the detergency, though they can also be irritating.

The inventive mixture of surfactants and additives may be placed in contact with the sore to be healed via a number of methods. A suitable method of applying the surfactant mixture to the sore to be treated is to soak the aqueous surfactant mixture into a cotton gauze pad and placing the wet gauze pad onto the sore. The gauze pad may be replaced as needed to follow medical protocols for wound dressing and healing. The gauze pad may be allowed to dry before removal as in a wet to dry pack wound treatment.

Other suitable methods of applying the surfactant mixture to the sore include spraying the aqueous surfactant mixture directly onto the sore to be treated or applying a thickened solution of the surfactants to the sore.

In another method, the surfactant mixture is added to water to give the desired concentration, placed in a water-stream-generating container such as a squirt bottle, and the water solution applied to the biofilm with mild pressure so that the surfactant solution flows into the wound over several seconds. A suitable flow rate is approximately one ounce of surfactant solution per second. A greater flow rate is acceptable, but should be adjusted so that the majority of the surfactant solution contacts the biofilm so that it may be physically removed by the action of the surfactants. The minimum flow rate is not defined, but since generally higher flow rates of surfactant solution result in greater biofilm removal rates, the flow rate should be maximized to reduce the time required and number of applications for complete biofilm removal. The surfactant solution application may be repeated as often as tolerated by the patient or as practical, up to several times per day.

There is no defined maximum or minimum amount of surfactant solution to be applied to a particular biofilm. In general, the larger the biofilm, the more treatment solution will be necessary. Longer application of more surfactant solution will remove more biofilm, and thus reduce the total treatment time. Removal of a biofilm internal to the body might preferably be completed by a single extended treatment to minimize exposure of internal organs to further infection. It is preferable to rinse the biofilm with water after application of the treatment mixture and allowing the biofilm to dry before reapplication.

The temperature of the treatment mixture is not critical, but if it is to be used on living tissue, the temperature should be adjusted close to body temperature to minimize any discomfort or damage.

The biofilms may be either internal or external to the body, and may be either on humans or animals or plants or hard surfaces. If the biofilm is on a hard surface the application rate and pressure may be increased to increase the biofilm removal rate.

EXAMPLES

Treatment Mixture A

The following ingredients were combined in the amounts shown. Care was taken to avoid air entrainment and foaming during the mixing operation.

| Ingredient | Amount (grams) | Concentration (gms of ingredient per gm of solution) delivered by supplier | solids (active ingredient gms) | Fraction of total solids in product |
| --- | --- | --- | --- | --- |
| (Glycereth-26 CAS 31694-55-0 | 183.13 | 1 | 183.13 | 0.16 |
| Sorbitol 70% solution | 52.32 | 0.7 | 36.63 | 0.03 |
| Sodium Laureth Sulfate CAS 68585-34-2 (26% solution in water) | 1465 | 0.26 | 380.90 | 0.33 |
| Sodium Lauryl Sulfoacetate (CAS 1847-58-1) and Disodium Laureth Sulfosuccinate (CAS 39354-45-5) = STEPAN MILD © LSB (25% solution in water) | 1465 | 0.25 | 366.25 | 0.32 |
| Cocodimethylaminopropylbetaine, CAS 70851-07-9, 35% in water | 366.25 | 0.35 | 128.19 | 0.11 |
| Imidazolidinyl urea (preservative) (Germal 115, CAS 39236-46-9) | 14.60 | 1 | 14.60 | 0.01 |
| USP grade water | 805.74 | | | |
| 20% tetrasodium EDTA dihydrate solution (CAS 64-02-8) to adjust pH to 7.4 | 212.75 | 0.2 | 42.55 | 0.04 |
| Lactic acid | — | | | |
| | 4564.79 | | 1152.24 | 1.00 |

The pH of the surfactant mixture was 7.4.

Other effective antimicrobial additives instead of imidazolidinyl urea include parabens, methylchloroisothiazolinone, and methylisothiazolinone. Bedsore treatment efficacy was excellent with no antimicrobial additive.

Example 1

Patient 1, a 72 year old male with Type 2 diabetes, developed a skin crack on his left heel that would not heal. After standard wound care methods the crack wound worsened resulting in treatment by a vascular surgeon wherein, after initial treatment cleared the lesion, an initial skin graft was done which failed after about one month. The lesion was cleaned again and another skin graft was applied which failed resulting in a 3 cm grossly infected left ankle and heel leading to a recommendation for amputation of the ankle and foot. The wound was then treated twice a day with various antibiotics and antibiotic creams and wet to dry packs with no improvement.

Treatment Mixture A was then applied twice per day via a squirt bottle to the sore after cleaning and before the application of a wet to dry pack. Healing commenced shortly after the start of the treatment with Treatment Mixture A, the sore gradually reduced in size, and the patient's sore was totally healed within about 12 weeks.

Example 2

Patient 2, a 57 year old male, had diabetes mellitus and severe neuropathy of his left foot and leg. His right leg had been amputated due to infection secondary to his diabetes illness. A 4×4 cm blister lesion was present on the plantar surface of his left foot. The lesion had purulent discharge. Amputation of the left foot was recommended.

Topical treatment of the lesion with Treatment Mixture A was begun along with a course of oral antibiotics. Just prior the treatment with Treatment Mixture A, he had purulent discharge and was debrided. One week later after treatment with Treatment Mixture A, the bedsore was healing with no drainage. After five more weeks of treatment, the wound was totally closed and after one additional week, the ulcer was healed and the patient was able to walk with his prosthetic leg as usual.

Example 3

Patient 3, a 22 year old male, was in poor health, smoked, and had a severe ulcer of over eighteen months duration on his leg. Physicians recommended treatment by a hem ipelvectomy. His ulcer was treated erratically with diluted Treatment Mixture A resulting in slow healing. Treatment frequency was then increased to daily, and healing accelerated.

Example 4

A 70 year old male with poor circulation in the lower limb and feet presented with an abscess on his foot that he had over a year. The abscess had developed an infection that was draining from his $1^{st}$ and $2^{nd}$ toe. He was provided with Treatment Mixture A which was diluted by adding 1 ml of Treatment Mixture A into 100 ml of saline solution and rinsing the sores with the diluted mixture. After about 3-4 weeks, both toes healed.

While the invention has been described with reference to the preferred embodiments other embodiments and improvements can be realized which are not specifically set forth but which are within the scope of the claimed invention as set fort in the claims appended hereto.

The invention claimed is:

1. A treatment mixture for treating biofilms on a human or animal comprising:

an effective amount of a salt of alkyleth sulfate defined by Formula I:

wherein:

$R^1$ is a branched or unbranched alkyl of 8-24 carbons;
$R^2$ is hydrogen or methyl;
n is an integer of 2 to 30; and
each $X^1$ is independently a counter ion;

an effective amount of at least one surfactant selected from the group consisting of a salt of alkyl sulfoacetate defined by Formula II:

$R^4OC(O)CH_2SO_3X^2$                                    Formula II wherein $R^4$ is a branched or unbranched alkyl of 8-24 carbons; and
$X^2$ is a counter ion;
and an effective amount of a salt of an alkyl sulfosuccinate defined by Formula III:

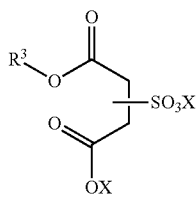

Formula III wherein:
$R^3$ is the branched or unbranched alkyl group of an alkyl alcohol with the alcohol hydrogen replaced with the sulfosuccinate wherein the alkyl has of 8-24 carbons, more preferably 10-18 carbons and most preferably 12-14 carbons;
X is a counter ion with the proviso that said treatment mixture does not comprise glucosides or phospholipids; and
comprising about 0.025-30% active ingredient in water.

2. The treatment mixture for treating biofilms on a human or animal of claim 1 wherein said $R^1$ comprises 10-18 carbons.

3. The treatment mixture for treating biofilms on a human or animal of claim 2 wherein said $R^1$ comprises 12-14 carbons.

4. The treatment mixture for treating biofilms on a human or animal of claim 1 wherein said n is an integer of preferably 4-10.

5. The treatment mixture for treating biofilms on a human or animal of claim 1 wherein said each $X^1$ is independently an alkali metal or ammonium.

6. The treatment mixture for treating biofilms on a human or animal of claim 5 wherein said each $X^1$ is independently selected from the group consisting of sodium and potassium and ammonium.

7. The treatment mixture for treating biofilms on a human or animal of claim 1 wherein said $R^4$ comprises 10-18 carbons.

8. The treatment mixture for treating biofilms on a human or animal of claim 7 wherein said $R^4$ comprises 12-14 carbons.

9. The treatment mixture for treating biofilms on a human or animal of claim 1 wherein said $X^2$ is an alkali metal or ammonium.

10. The treatment mixture for treating biofilms on a human or animal of claim 9 wherein said $X^2$ is selected from the group consisting of sodium and potassium and ammonium.

11. The treatment mixture for treating biofilms on a human or animal of claim 1 wherein said $R^3$ comprises 10-18 carbons.

12. The treatment mixture for treating biofilms on a human or animal of claim 11 wherein said $R^3$ comprises 12-14 carbons.

13. The treatment mixture for treating biofilms on a human or animal of claim 1 wherein said X is an alkali metal or ammonium.

14. The treatment mixture for treating biofilms on a human or animal of claim 13 wherein said X is selected from the group consisting of sodium and potassium and ammonium.

15. The treatment mixture for treating biofilms on a human or animal of claim 1 wherein said salt of alkylether sulfate is sodium laureth sulfate.

16. The treatment mixture for treating biofilms on a human or animal of claim 1 wherein said salt of alkyl sulfoacetate is disodium lauryl sulfoacetate.

17. The treatment mixture for treating biofilms on a human or animal of claim 1 wherein said salt of an alkyl sulfosuccinate is disodium lauryl sulfosuccinate.

18. The treatment mixture for treating biofilms on a human or animal of claim 1 comprising both said salt of alkyl sulfoacetate and said salt of an alkyl sulfosuccinate.

19. The treatment mixture for treating biofilms on a human or animal of claim 1 wherein said treatment mixture is selected from a liquid, a gel and a foam.

20. The treatment mixture for treating biofilms on a human or animal of claim 1 further comprising nonionic or amphoteric surfactants.

21. A method for the removal of bacterial biofilms comprising:
applying a treatment mixture to said biofilm wherein said treatment mixture comprises:
an effective amount of a salt of alkyleth sulfate defined by Formula I:

$R^1—(OCHR^2CH_2)n—OSO_3X^1$                      Formula I wherein:
$R^1$ is a branched or unbranched alkyl of 8-24 carbons;
$R^2$ is hydrogen or methyl;
n is an integer of 2 to 30; and
each $X^1$ is independently a counter ion;
an effective amount at least one surfactant selected from the group consisting of a salt of alkyl sulfoacetate defined by Formula II:

$R^4OC(O)CH_2SO_3X^2$                                    Formula II wherein $R^4$ is a branched or unbranched alkyl of 8-24 carbons; and
$X^2$ is a counter ion;
and a salt of an alkyl sulfosuccinate defined by Formula III:

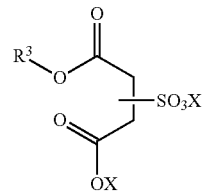

Formula III wherein:
$R^3$ is the branched or unbranched alkyl group of an alkyl alcohol with the alcohol hydrogen replaced with the sulfosuccinate wherein the alkyl has of 8-24 carbons, more preferably 10-18 carbons and most preferably 12-14 carbons; and
X is a counter ion;

allowing said treatment mixture to remain in contact with said biofilm until dry;
rinsing with water; and
re-applying a treatment mixture to said biofilm.

22. The method for the removal of bacterial biofilms of claim 21 wherein said biofilm is integral to a bedsore.

23. The method for the removal of bacterial biofilms of claim 21 in which application of the surfactant solution to the wound is chosen from the group comprising a spray, soaking on a gauze pad, application of a gel, etc.

24. The method for the removal of bacterial biofilms of claim 21 wherein said $R^1$ comprises 10-18 carbons.

25. The method for the removal of bacterial biofilms of claim 24 wherein said $R^1$ comprises 12-14 carbons.

26. The method for the removal of bacterial biofilms of claim 21 wherein said n is an integer of preferably 4-10.

27. The method for the removal of bacterial biofilms of claim 21 wherein said each $X^1$ is independently an alkali metal or ammonium.

28. The method for the removal of bacterial biofilms of claim 27 wherein said each $X^1$ is independently selected from the group consisting of sodium and potassium and ammonium.

29. The method for the removal of bacterial biofilms of claim 21 wherein said $R^4$ comprises 10-18 carbons.

30. The method for the removal of bacterial biofilms of claim 21 wherein said $X^2$ is an alkali metal or ammonium.

31. The method for the removal of bacterial biofilms of claim 30 wherein said $R^4$ comprises 12-14 carbons.

32. The method for the removal of bacterial biofilms of claim 30 wherein said $X^2$ is selected from the group consisting of sodium and potassium and ammonium.

33. The method for the removal of bacterial biofilms of claim 21 wherein said $R^3$ comprises 10-18 carbons.

34. The method for the removal of bacterial biofilms of claim 33 wherein said $R^3$ comprises 12-14 carbons.

35. The method for the removal of bacterial biofilms of claim 21 wherein said X is an alkali metal or ammonium.

36. The method for the removal of bacterial biofilms of claim 35 wherein said X is selected from the group consisting of sodium and potassium and ammonium.

37. The method for the removal of bacterial biofilms of claim 21 wherein said salt of alkyleth sulfate is sodium laureth sulfate.

38. The method for the removal of bacterial biofilms of claim 21 wherein said salt of alkyl sulfoacetate is disodium lauryl sulfoacetate.

39. The method for the removal of bacterial biofilms of claim 21 wherein said salt of an alkyl sulfosuccinate is disodium lauryl sulfosuccinate.

40. The method for the removal of bacterial biofilms of claim 21 comprising both said salt of alkyl sulfoacetate and said salt of an alkyl sulfosuccinate.

41. The method for the removal of bacterial biofilms of claim 21 wherein said treatment mixture comprises about 0.025-30% active ingredient in water.

42. The method for the removal of bacterial biofilms of claim 21 wherein said treatment mixture is selected from a liquid, a gel and a foam.

43. The method for the removal of bacterial biofilms of claim 21 further comprising nonionic or amphoteric surfactants.

* * * * *